(12) United States Patent
Clark et al.

(10) Patent No.: US 9,486,622 B2
(45) Date of Patent: Nov. 8, 2016

(54) FIXATION AND STRAIN RELIEF ELEMENT FOR TEMPORARY THERAPY DELIVERY DEVICE

(71) Applicant: Cardiac Pacemakers, Inc., St. Paul, MN (US)

(72) Inventors: Bryan A. Clark, Forest Lake, MN (US); Timothy R. Jackson, Minneapolis, MN (US); Lili Liu, Maple Grove, MN (US); Arthur J. Foster, Blaine, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 129 days.

(21) Appl. No.: 14/030,741

(22) Filed: Sep. 18, 2013

(65) Prior Publication Data

US 2014/0128948 A1    May 8, 2014

Related U.S. Application Data

(60) Provisional application No. 61/723,996, filed on Nov. 8, 2012.

(51) Int. Cl.
*A61N 1/05* (2006.01)

(52) U.S. Cl.
CPC .................. *A61N 1/0558* (2013.01)

(58) Field of Classification Search
CPC .......................... A61N 1/0558; A61N 1/0504
USPC .......................................................... 607/116
See application file for complete search history.

(56) References Cited

U.S. PATENT DOCUMENTS

| | | | |
|---|---|---|---|
| 4,254,774 A | * | 3/1981 | Boretos ............ A61M 25/1027 604/271 |
| 4,266,552 A | | 5/1981 | Dutcher et al. |
| 4,276,882 A | | 7/1981 | Dickhudt et al. |
| 4,287,891 A | | 9/1981 | Peters |
| 4,301,815 A | | 11/1981 | Doring |
| 4,387,727 A | | 6/1983 | Sandstrom |
| 4,409,994 A | | 10/1983 | Doring |
| 4,437,475 A | | 3/1984 | White |

(Continued)

FOREIGN PATENT DOCUMENTS

| | | |
|---|---|---|
| EP | 1314449 A2 | 5/2003 |
| EP | 2275169 A1 | 1/2011 |

(Continued)

OTHER PUBLICATIONS

Pacing Lead Stabilizer with Modified Slit Geometry, Technical Disclosure from www.ip.com, No. IPCOM000130753D, published Nov. 3, 2005, full document available at http://www.ip.com/pubview/IPCOM000125732D,6 pages.

(Continued)

*Primary Examiner* — Paula J Stice
(74) *Attorney, Agent, or Firm* — Faegre Baker Daniels LLP (57) ABSTRACT

A temporary neurostimulation lead may be secured relative to patient using a fixation device. The fixation device may include an attachment portion that is configured to be releasably fixated to the patient and a lead fixation portion that is configured to secure the temporary neurostimulation lead. The fixation device can be adhesively fixated to the patient via the attachment portion and the temporary neurostimulation lead can be fixated to the lead fixation portion of the fixation device.

19 Claims, 10 Drawing Sheets

(56) References Cited

U.S. PATENT DOCUMENTS

| | | |
|---|---|---|
| 4,442,840 A | 4/1984 | Wojciechowicz, Jr. |
| 4,516,584 A | 5/1985 | Garcia |
| 4,517,971 A * | 5/1985 | Sorbonne ............. A61M 25/02 128/879 |
| 4,519,404 A | 5/1985 | Fleischhacker |
| 4,538,623 A | 9/1985 | Proctor et al. |
| 4,550,737 A | 11/1985 | Osypka |
| 4,553,961 A | 11/1985 | Pohndorf et al. |
| 4,585,013 A | 4/1986 | Harris |
| 4,613,329 A | 9/1986 | Bodicky |
| 4,615,472 A | 10/1986 | Nash |
| 4,672,979 A | 6/1987 | Pohndorf |
| 4,676,782 A | 6/1987 | Yamamoto et al. |
| 4,683,895 A | 8/1987 | Pohndorf |
| 4,768,523 A | 9/1988 | Cahalan et al. |
| 4,796,643 A | 1/1989 | Nakazawa et al. |
| 4,906,233 A | 3/1990 | Moriuchi et al. |
| 5,036,862 A | 8/1991 | Pohndorf |
| 5,107,856 A | 4/1992 | Kristiansen et al. |
| 5,129,405 A | 7/1992 | Milijasevic et al. |
| 5,152,298 A | 10/1992 | Kreyenhagen et al. |
| 5,242,431 A | 9/1993 | Kristiansen |
| 5,257,975 A | 11/1993 | Foshee |
| 5,273,053 A | 12/1993 | Pohndorf |
| 5,366,496 A | 11/1994 | Dahl et al. |
| 5,376,108 A | 12/1994 | Collins et al. |
| 5,423,763 A | 6/1995 | Helland et al. |
| 5,476,493 A | 12/1995 | Muff |
| 5,484,445 A | 1/1996 | Knuth |
| 5,549,619 A | 8/1996 | Peters et al. |
| 5,583,319 A | 12/1996 | Lieurance |
| 5,584,874 A | 12/1996 | Rugland et al. |
| 5,603,730 A | 2/1997 | Romkee |
| 5,628,780 A | 5/1997 | Helland et al. |
| 5,674,273 A | 10/1997 | Helland |
| 5,683,403 A | 11/1997 | Adams et al. |
| 5,683,446 A | 11/1997 | Gates |
| 5,709,644 A | 1/1998 | Bush |
| 5,735,891 A | 4/1998 | White |
| 5,746,722 A | 5/1998 | Pohndorf et al. |
| 5,800,402 A * | 9/1998 | Bierman ............... A61M 25/02 128/DIG. 26 |
| 5,824,032 A | 10/1998 | Belden |
| 5,827,296 A | 10/1998 | Morris et al. |
| 5,843,146 A | 12/1998 | Cross, Jr. |
| 5,871,528 A | 2/1999 | Camps et al. |
| 5,876,429 A | 3/1999 | Schroeppel |
| 5,957,968 A | 9/1999 | Belden et al. |
| 6,002,969 A | 12/1999 | Machek et al. |
| 6,134,477 A | 10/2000 | Knuteson |
| 6,173,206 B1 | 1/2001 | Shchervinsky |
| 6,259,953 B1 | 7/2001 | Lucchesi et al. |
| 6,463,334 B1 | 10/2002 | Flynn et al. |
| 6,473,654 B1 | 10/2002 | Chinn |
| 6,554,802 B1 | 4/2003 | Pearson et al. |
| 6,592,553 B2 | 7/2003 | Zhang et al. |
| 6,643,550 B2 | 11/2003 | Westlund et al. |
| 6,895,277 B2 | 5/2005 | Westlund et al. |
| 6,901,287 B2 | 5/2005 | Davis et al. |
| 6,912,423 B2 | 6/2005 | Ley et al. |
| 6,915,169 B2 | 7/2005 | Flynn et al. |
| 6,921,295 B2 | 7/2005 | Sommer et al. |
| 6,985,777 B2 | 1/2006 | Tsuboi et al. |
| 7,082,337 B2 | 7/2006 | Sommer et al. |
| 7,090,660 B2 | 8/2006 | Robert et al. |
| 7,184,841 B1 | 2/2007 | Bodner et al. |
| 7,218,972 B2 | 5/2007 | Rodriguez |
| 7,242,986 B2 | 7/2007 | Rodriguez |
| 7,248,930 B1 | 7/2007 | Woloszko et al. |
| 7,398,125 B2 | 7/2008 | Osypka et al. |
| 7,747,334 B2 | 6/2010 | Bly et al. |
| 7,765,015 B2 | 7/2010 | Johnson et al. |
| 7,806,886 B2 | 10/2010 | Kanderian, Jr. et al. |
| 7,914,582 B2 | 3/2011 | Felt et al. |
| 8,000,811 B2 | 8/2011 | Hill |
| 8,126,569 B2 | 2/2012 | Rivard et al. |
| 8,271,096 B2 | 9/2012 | Rivard et al. |
| 2002/0133121 A1* | 9/2002 | Bierman ..................... 604/174 |
| 2003/0050668 A1 | 3/2003 | Lee |
| 2003/0130616 A1 | 7/2003 | Steil et al. |
| 2003/0195600 A1 | 10/2003 | Tronnes et al. |
| 2003/0220678 A1 | 11/2003 | Tronnes et al. |
| 2004/0059403 A1 | 3/2004 | Massullo |
| 2004/0093052 A1 | 5/2004 | Westlund et al. |
| 2004/0143216 A1 | 7/2004 | Douglas et al. |
| 2004/0254623 A1 | 12/2004 | Rodriguez et al. |
| 2005/0080470 A1 | 4/2005 | Westlund et al. |
| 2005/0137664 A1 | 6/2005 | Sommer et al. |
| 2005/0177220 A1 | 8/2005 | Iaizzo et al. |
| 2005/0202703 A1 | 9/2005 | Westlund et al. |
| 2005/0267557 A1 | 12/2005 | Flynn et al. |
| 2006/0235484 A1 | 10/2006 | Jaax et al. |
| 2006/0264803 A1 | 11/2006 | Lui et al. |
| 2007/0078399 A1 | 4/2007 | Olson |
| 2007/0156216 A1 | 7/2007 | McAuliffe et al. |
| 2007/0225784 A1 | 9/2007 | Bly et al. |
| 2007/0282412 A1 | 12/2007 | Soltis et al. |
| 2007/0282414 A1 | 12/2007 | Soltis et al. |
| 2007/0282415 A1 | 12/2007 | Tockman et al. |
| 2007/0293922 A1 | 12/2007 | Soltis et al. |
| 2008/0228251 A1 | 9/2008 | Hill |
| 2008/0262587 A1 | 10/2008 | Flynn et al. |
| 2008/0262588 A1 | 10/2008 | Zarembo et al. |
| 2009/0125058 A1 | 5/2009 | Bodner et al. |
| 2009/0125059 A1 | 5/2009 | Verzal et al. |
| 2009/0125060 A1 | 5/2009 | Rivard et al. |
| 2009/0125061 A1 | 5/2009 | Rivard et al. |
| 2009/0326473 A1 | 12/2009 | Rosenberg et al. |
| 2010/0016801 A1 | 1/2010 | Rosenberg et al. |
| 2010/0114034 A1 | 5/2010 | Wright et al. |
| 2011/0009935 A1* | 1/2011 | Kane et al. .................... 607/116 |
| 2011/0046669 A1* | 2/2011 | Goraltchouk ..... A61B 17/06166 606/228 |
| 2012/0029335 A1 | 2/2012 | Sudam et al. |
| 2012/0071959 A1 | 3/2012 | Helgesson |
| 2012/0330354 A1 | 12/2012 | Kane et al. |
| 2013/0138200 A1 | 5/2013 | Mayberry et al. |
| 2013/0158640 A1 | 6/2013 | Soltis et al. |
| 2014/0121739 A1 | 5/2014 | Fuhs et al. |
| 2015/0352352 A1 | 12/2015 | Soltis et al. |

FOREIGN PATENT DOCUMENTS

| | | |
|---|---|---|
| WO | WO2006116454 A2 | 11/2006 |
| WO | WO2007024164 A1 | 1/2007 |

OTHER PUBLICATIONS

Suture Sleeve with Removable Fins, Technical Disclosure from www.ip.com, No. IPCOM000125732D, published Jun. 15, 2005, full document available at http://www.ip.comIpubviewIIPCOM000125732D, 4 pages.

International Search Report and Written Opinion issued in PCT/US2013/067138, mailed Mar. 20, 2014, 13 pages.

* cited by examiner

FIXATION AND STRAIN RELIEF ELEMENT FOR TEMPORARY THERAPY DELIVERY DEVICE

CROSS-REFERENCE TO RELATED APPLICATIONS

This application claims the benefit under 35 U.S.C. section 119(e) to U.S. provisional application No. 61/723,996 entitled "FIXATION AND STRAIN RELIEF ELEMENT FOR TEMPORARY THERAPY DELIVERY DEVICE", filed on Nov. 8, 2012, which is herein incorporated by reference in its entirety.

TECHNICAL FIELD

The present invention relates to implantable leads. More specifically, the invention relates to devices and methods for fixating implantable leads such as temporary neurostimulation leads.

BACKGROUND

Temporary implantable leads are often used to evaluate the usefulness of neurostimulation prior to implanting a chronically implantable system within a patient. In some instances, as a treatment for urinary incontinence, patients may be implanted with a trial percutaneous nerve evaluation lead in order to evaluate the efficacy of sacral nerve stimulation for a particular patient. In some cases, the trial lead may be introduced from the posterior side of the sacrum, through a foramen thereof, and into the vicinity of the sacral nerves in order to place an electrode into close proximity with the sacral nerves. At the percutaneous entry point on the patient's back, the lead can be coiled and then affixed to the skin with a small transparent dressing.

While there are advantages to using temporary medical leads to evaluate the potential performance of neurostimulation, there are several potential complications. Examples of potential complications include lead migration and infection. Because, in many cases, the trial lead exits the skin and is only taped to the back of the patient, the lead can be accidently displaced by the patient as they move about performing daily activities. In order to reduce the risks of infection, the time period in which the lead remains implanted is often-times reduced.

SUMMARY

Example 1 is a method of securing a temporary neurostimulation lead relative to an entry point on a patient. The temporary neurostimulation lead is implanted within the patient such that the temporary neurostimulation lead extends through the entry point and is disposed proximate a desired nerve within the patient. A fixation device is advanced over the temporary neurostimulation lead to a position proximate the entry point. The fixation device includes an attachment portion configured to be releasably fixated to the patient and a lead fixation portion configured to secure the temporary neurostimulation lead. The attachment portion of the fixation device is adhesively fixated to the patient and the temporary neurostimulation lead is fixated to the lead fixation portion of the fixation device.

Example 2 includes Example 1 and further specifies that the lead fixation portion includes a curved channel formed in an upper surface of the lead fixation portion. Example 2 specifies that fixating the temporary neurostimulation lead to the lead fixation portion of the fixation device includes fitting the temporary neurostimulation lead into the curved channel.

Example 3 includes Example 1 and further specifies that the lead fixation portion includes one or more raised portions that are configured to frictionally engage a spiral-cut strain relief element. Example 3 specifies that fixating the temporary neurostimulation lead to the lead fixation portion of the fixation device includes wrapping the temporary neurostimulation lead within the spiral-cut strain relief and snapping the spiral-cut strain relief into the one or more raised portions.

Example 4 includes Example 1 and further specifies that the lead fixation portion includes an upper surface and one or more resilient fingers extending from the upper surface and biased into contact with the upper surface. Example 4 specifies that fixating the temporary neurostimulation lead to the lead fixation portion of the fixation device includes lifting each of the one or more resilient fingers, placing the temporary neurostimulation lead under each of the one or more resilient fingers and allowing each of the one or more resilient fingers to return to their biased position in contact with the upper surface.

Example 5 includes Example 1 and further specifies that the lead fixation portion includes a resilient polymeric body including a lumen therethrough to accommodate the temporary neurostimulation lead. Example 5 specifies that advancing the fixation device over the temporary neurostimulation lead to a position proximate the entry point includes advancing the fixation device over the temporary neurostimulation lead with the temporary neurostimulation lead extending through the lumen.

Example 6 includes Example 5 and further specifies that fixating the temporary neurostimulation lead to the lead fixation portion of the fixation device includes disposing an external clamp over the resilient polymeric body to compress the resilient polymeric body into frictional contact with the temporary neurostimulation lead.

Example 7 includes Example 5 and further specifies that the resilient fixation portion includes an upper portion that is rotatable relative to a lower portion, and that the lumen is defined at least in part by polymeric bands extending between the upper portion and the lower portion. Example 7 specifies that fixating the temporary neurostimulation lead to the lead fixation portion of the fixation device includes rotating the upper portion relative to the lower portion in order to tighten the polymeric bands around the temporary neurostimulation lead and securing the upper portion relative to the lower portion to maintain the polymeric bands in their tightened configuration.

Example 8 includes Example 5 and further specifies that the lead fixation portion includes an under skin fixation feature and an activation portion that is operably connected to the under skin fixation feature. Example 8 specifies that adhesively fixating the attachment portion of the fixation device to the patient further includes squeezing the activation portion to move the under skin fixation feature into a configuration that permits the under skin fixation feature to be inserted under the skin, inserting the under skin fixation feature under the skin and releasing the activation portion to permit the under skin fixation feature to return to a biased position that anchors the under skin fixation feature under the skin.

Example 9 is a fixation device configured to releasably secure a temporary neurostimulation lead relative to an entry point on a patient. The fixation device includes a polymeric device body having a lower surface and an upper surface, a dermatologically safe adhesive disposed on the lower surface for releasably securing the fixation device to the patient proximate the entry point and a lead fixation structure formed within the upper surface, the lead fixation structure configured to releasably secure the temporary neurostimulation lead.

Example 10 includes Example 9 and further specifies that the lead fixation structure includes a curved channel configured to releasably secure a temporary neurostimulation lead therein.

Example 11 includes Example 9 and further specifies that the lead fixation structure includes one or more raised portions that are configured to frictionally engage a spiral-cut strain relief element.

Example 12 includes Example 11 and further specifies that the fixation device includes a spiral-cut strain relief element.

Example 13 includes Example 9 and further specifies that the lead fixation structure includes one or more resilient fingers that extend from the upper surface and are biased into contact with the upper surface.

Example 14 includes Example 9 and further specifies that the fixation device includes an external clamp that is configured to clamp onto the lead fixation structure to releasably secure the temporary neurostimulation lead.

Example 15 includes Example 9 and further specifies that the polymeric device body includes an upper portion that is rotatable relative to a lower portion, with polymeric bands extending between the upper portion and the lower portion. Example 15 specifies that rotating the upper portion relative to the lower portion enables the polymeric bands to tighten around the temporary neurostimulation lead.

Example 16 includes Example 9 and further specifies that the fixation device includes under an skin fixation element and an activation portion that is operably connected to the under skin fixation element. Example 16 specifies that squeezing the activation portion moves the under skin fixation element into a configuration that permits the under skin fixation element to be inserted under the skin and releasing the activation portion permits the under skin fixation element to return to a biased position that anchors the under skin fixation element under the skin.

Example 17 is a fixation device that is configured to releasably secure a temporary neurostimulation lead relative to an entry point on a patient. The fixation device includes a polymeric device body having a lower surface and an upper surface and a dermatologically safe adhesive disposed on the lower surface for releasably securing the fixation device to the patient proximate the entry point. The fixation device includes a spiral-cut strain relief element including an elongate body and a spiral groove formed within the elongate body, the spiral groove configured to accommodate the temporary neurostimulation lead therein. A pair of raised portions are molded into the upper surface, the pair of raised portions being configured to frictionally engage the spiral-cut strain relief element.

Example 18 includes Example 17 and further specifies that the fixation device includes a peel away layer disposed on the dermatologically safe adhesive in order to protect the adhesive.

Example 19 includes Example 17 and further specifies that the pair of raised portions are integrally molded as part of the polymeric device body.

Example 20 includes Example 17 and further specifies that the polymeric device body includes an elongate slot formed within the polymeric device body such that the elongate slot permits the fixation device to be slid laterally onto the temporary neurostimulation lead.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

Figure 1:
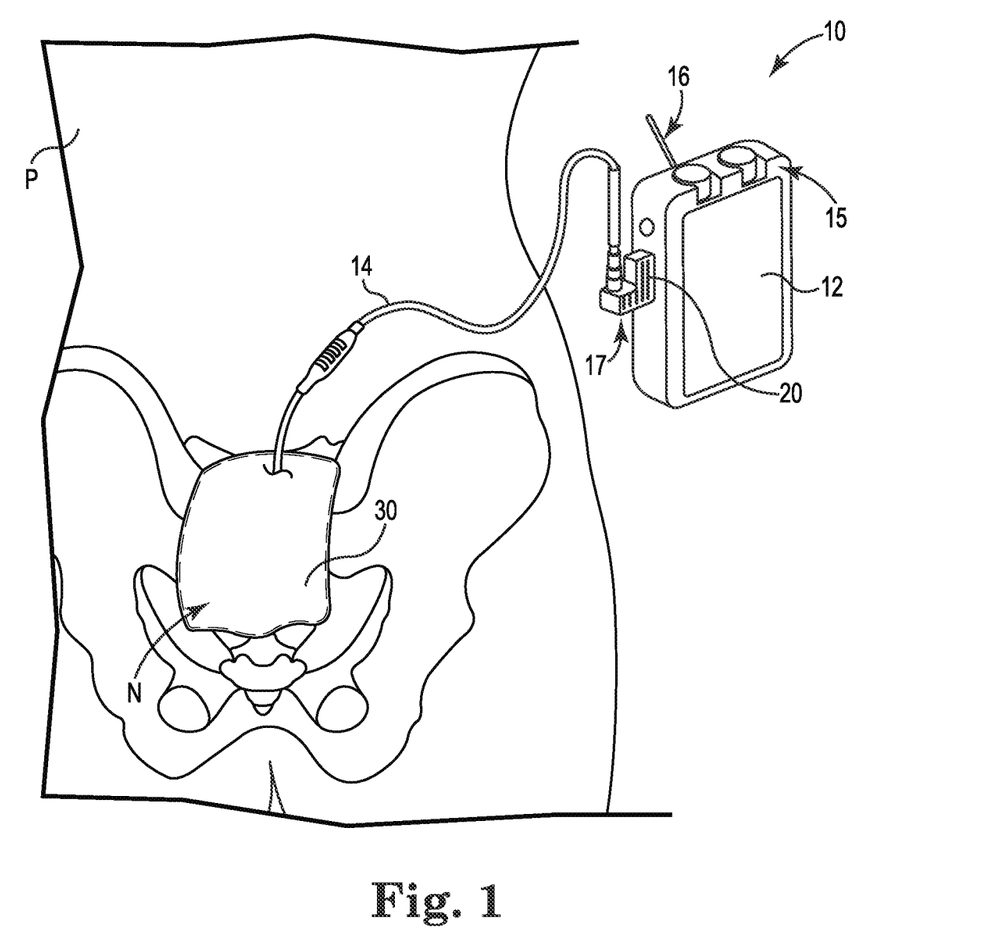
FIG. 1 illustrates an embodiment of a temporary neurostimulation lead positioned proximate the sacral nerves of a patient.

FIG. 1 illustrates an embodiment of an electrical stimulation system 10 including a control module (e.g., stimulator or pulse generator) 12 and a temporary implantable medical device lead 14 coupled to the control module 12. In some embodiments, the electrical stimulation system 10 is a peripheral nerve evaluation (PNE) stimulation system, which allows temporary implantation of a lead at a nerve site to test whether neurostimulation at the site improves the condition being treated. In the embodiment shown, the lead 14 is implanted proximate a sacral nerve N of a patient P. In other embodiments, the electrical stimulation system 10 is configured to provide stimulation to other nerve bundles or other portions or systems of the body. While illustrated and described as a temporary lead, the lead 14 may alternatively be configured as a chronically implanted lead.

The control module 12 is configured to deliver stimulation signals to the lead 14 and/or receive electrical signals sensed by the lead 14. In some embodiments, the control module 12 is an externally carried or worn device. The control module 12 may include external controls 15 that allow the clinician to set characteristics (e.g., periodicity, frequency, amplitude, etc.) of the therapy delivered to the sacral nerve N via the lead 14. The control module 12 may also include an antenna 16 configured to communicate with an external device (e.g., programmer), for example to receive programming related to therapy delivery.

The lead 14 includes a proximal end 17 and a distal end (not illustrated). In some embodiments, the distal end of the lead 14 includes a plurality of electrodes (not shown) positioned proximate to the sacral nerve N. The lead 14 may be introduced from the posterior side of the sacrum, through a foramen thereof, and into the region of the sacral nerves and positioned such that a plurality of electrodes at the distal end is in close vicinity to the sacral nerve N for electrical stimulation. At the proximal end 17, the lead includes a connector 20 configured to mechanically and electrically couple the lead 14 to the control module 12. The connector 20 may include a plurality of contacts that electrically couple the electrodes at the distal end (not shown) of the lead 14 to the electrical components of the control module 12 via a conductor extending through the lead 14.

At the percutaneous entry site on the back of the patient P, the lead 14 may be secured to the patient P via a schematically shown fixation device 30. As will be discussed with respect to subsequent Figures, the fixation device 30 may take several different forms, but share particular features. For example, the fixation device 30 is configured to be releasably securable to the patient P. The fixation device 30 is configured to releasably secure the lead 14 to the patient P while permitting subsequent removal of the lead 14 from the fixation device 30. In some embodiments, the fixation device is configured to seal against the lead 14 and the patient's skin in order to reduce the possibilities of infection.

Figure 2:
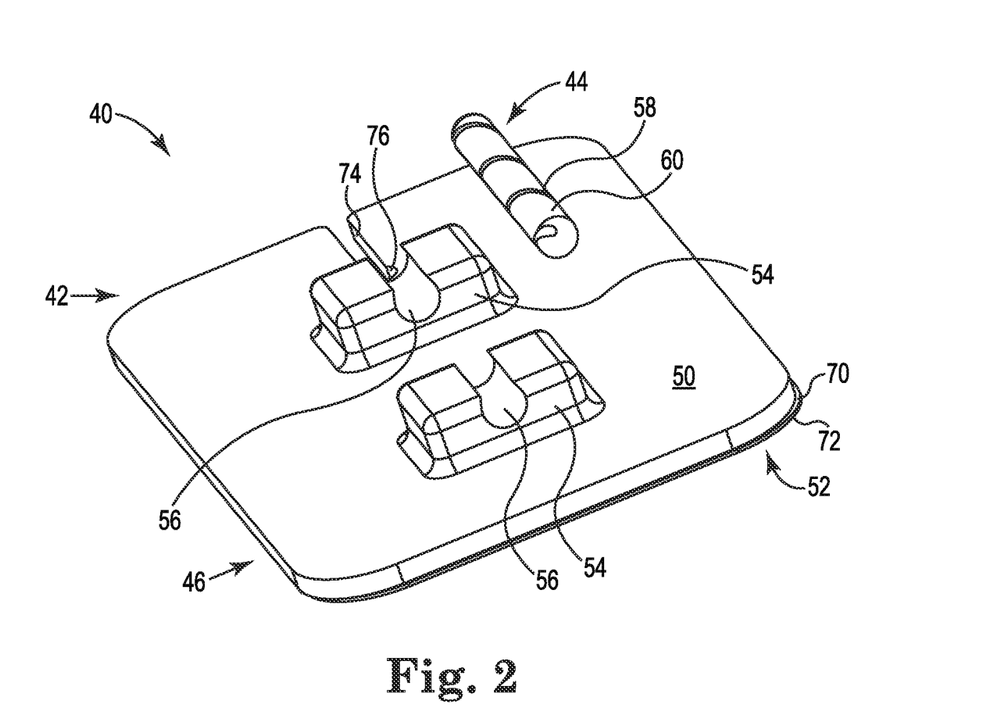
FIG. 2 is a perspective view of a fixation device in accordance with embodiments of the present invention.

FIG. 2 is a perspective view of a fixation device 40 that includes a polymeric device body 42 and a spiral-cut strain relief member 44. While the polymeric device body 42 is illustrated as having a rectangular profile, it will be appreciated that in some embodiments the polymeric device body 42 may have a square profile, a round profile or another, irregular, shape. The polymeric device body 42 includes a base 46 having an upper surface 50 and a lower surface 52. In some embodiments, the lower surface 52 includes an adhesive coating or layer 70 that can be used to secure the polymeric device body 42 onto the patient P proximate the entry point. Any suitable dermatologically safe adhesive can be used. In some embodiments, a peel-away layer 72 may be disposed over the adhesive layer 70 to protect the adhesive layer 70 until the fixation device 40 is about to be used. In some embodiments, the base 46 may be configured to accommodate sutures to provide additional securement.

In the illustrated embodiment, a pair of raised portions 54 are molded into the upper surface 50 and extend above the upper surface 50. While a pair of raised portions 54 are shown, it will be appreciated that in some embodiments the fixation device 40 may include only a single raised portion 54 or may include three or more raised portions 54. In some embodiments, the pair of raised portions 54 are integrally molded as a unitary part of the polymeric device body 42.

The pair of raised portions 54 may include regular or irregular-shaped cut-outs for accommodating the lead 14. In the illustrated embodiment, the pair of raised portions 54 each include a cylindrical cut-out portion 56 that is sized to frictionally engage with the spiral-cut strain relief member 44. In some embodiments, the cylindrical cut-out portions 56 may have a semi-circular shape having a radius that is slightly less than a corresponding diameter of the spiral-cut strain relief member 44 such that the spiral-cut strain relief member 44 frictionally engages with the cut-out portions 56. The cut-out portions 56 may have a radius of circumference that is, for example, from about 95 to about 99.9 percent of the diameter of the spiral-cut strain relief member 44. In some embodiments, the cut-out portions 56 may have an upper opening that is smaller than a diameter of the cut-out portions 56. For example, the cut-out portions 56 may have an upper opening that is about 75 to 95 percent of a diameter of the cut-out portions 56. In some embodiments, the raised portions 54 may have a cut-out portion having a triangular shape, which may provide up to three contact points between the lead 14 and the raised portion 54, or a diamond shape, which may provide up to four contact points between the lead 14 and the raised portion 54.

The spiral-cut strain relief member 44 is configured to permit the lead 14 to be wound around the spiral-cut strain relief member 44. In some embodiments, as illustrated, the spiral-cut strain relief member 44 includes a spirally arranged groove 58 that is cut or otherwise formed into an outer surface 60 of the spiral-cut strain relief member 44. The spirally arranged groove 58 can have a depth that is in the range of about 10 percent to about 40 percent of a diameter of the spiral-cut strain relief member 44. The spirally arranged groove 58 can have a width that is about the same or slightly less than a diameter of the lead 14 such that the lead 14 can easily be wound into the spirally arranged groove 58 yet the groove 58 can provide at least some resistance to removal of the lead 14.

In some embodiments, the polymeric device body 42 includes a slot 74 having an enlarged portion 76. The enlarged portion 76 can be sized to easily accommodate the lead 14. The slot 74 may be a width that is somewhat less than the lead 14 yet can permit the lead 14 to be advanced into the enlarged portion 76 by, for example, bending the polymeric device body 42 to effectively and temporarily enlarge the slot 74. In some embodiments, the polymeric device body 42 may include a hole for the lead 14 to pass through, but may not include the slot 74.

Figure 3:
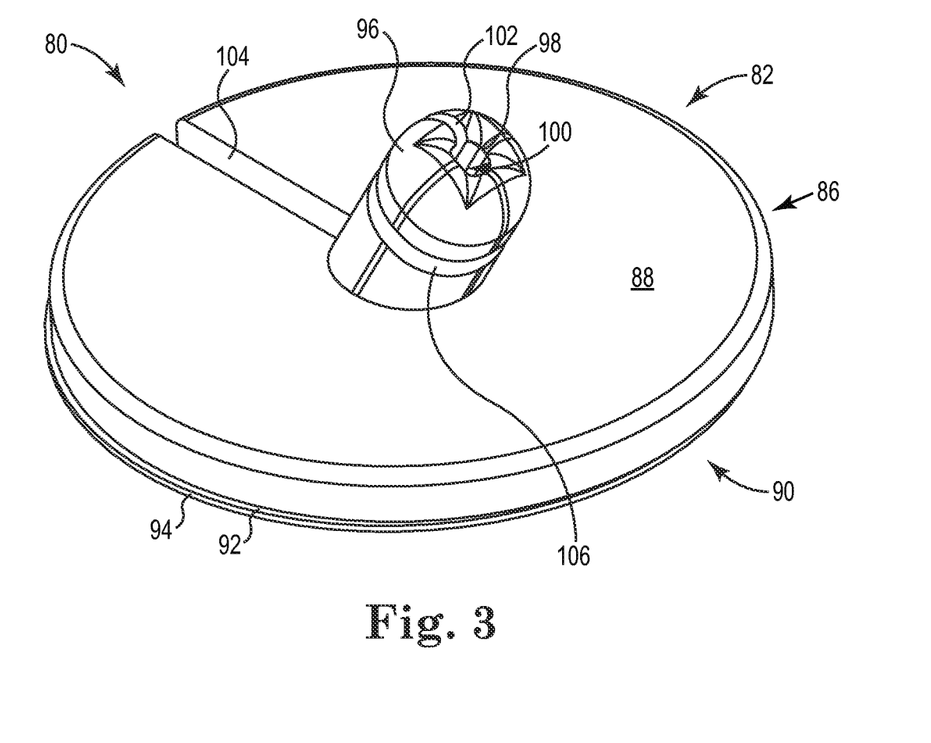
FIG. 3 is a perspective view of a fixation device in accordance with embodiments of the present invention.

FIG. 3 is a perspective view of a fixation device 80 that includes a polymeric device body 82. While the polymeric device body 82 is illustrated as having a round profile, it will be appreciated that in some embodiments the polymeric device body 82 may have a square profile, a rectangular profile or another, irregular, shape. The polymeric device body 82 includes a base 86 having an upper surface 88 and a lower surface 90. In some embodiments, the lower surface 90 includes an adhesive coating or layer 92 that can be used to secure the polymeric device body 82 onto the patient P proximate the entry point. Any suitable dermatologically safe adhesive can be used. In some embodiments, a peel-away layer 94 may be disposed over the adhesive layer 92 to protect the adhesive layer 92 until the fixation device 80 is about to be used. In some embodiments, the base 86 may be configured to accommodate sutures to provide additional securement.

The fixation device 80 includes a tower portion 96 that extends above the upper surface 88 of the polymeric device body 82. While the tower portion 96 can be seen as forming a particular angle with the upper surface 88, it will be appreciated that in some embodiments the tower portion 96 may form an acute angle with the upper surface 88 that is in the range of about 5 degrees to about 90 degrees. In some embodiments, reducing the angle formed between the tower portion 96 and the upper surface 88 provides the fixation device 80 with a lower profile that can fit better under a patient's clothes, for example.

The tower portion 96 includes an aperture 98 that is sized to accommodate the lead 14 therein and that leads to a lumen 100 that extends through the tower portion 96. In some embodiments, as illustrated, the tower portion 96 includes a slot 102 that is in communication with the lumen 100 and may facilitate placement and advancement of the lead 14 through the tower portion 96. In some embodiments, the polymeric device body 82 includes a slot 104. The slot 104 may be sized to accommodate the lead 14.

In some embodiments, the tower portion 96 can be tightened against the lead 14 by placing an external clamp such as a spring clip around the tower portion 96. In some embodiments, as illustrated, the tower portion 96 includes an annular reduced diameter portion 106 that facilitates placement of an external clamp.

Figure 4:
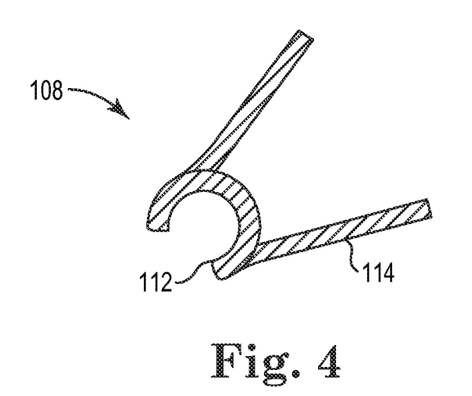
FIG. 4 is a schematic view of an external clamp in accordance with embodiments of the present invention.
Figure 5:
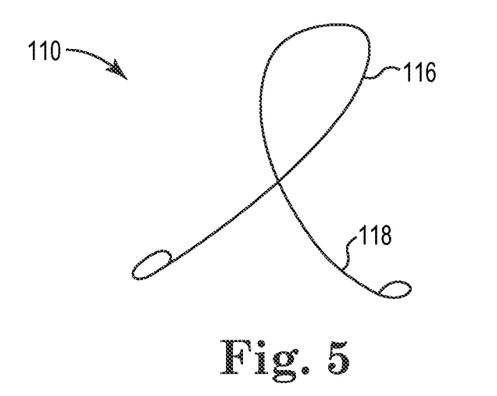
FIG. 5 is a schematic view of an external clamp in accordance with embodiments of the present invention.

FIGS. 4 and 5 provide illustrative but non-limiting examples of external clamps 108 and 110, respectively. The external clamp 108 includes a clamping portion 112 and a handle portion 114. The clamping portion 112 may, for example, be moved into a position in which the clamping portion 112 fits over the annular reduced diameter portion 106 by squeezing together the handle portion 114. The external clamp 110 is a spring clip and includes a clamping portion 116 and a handle portion 118. The clamping portion 116 can be temporarily enlarged in diameter by squeezing together the handle portion 118.

Figure 6:
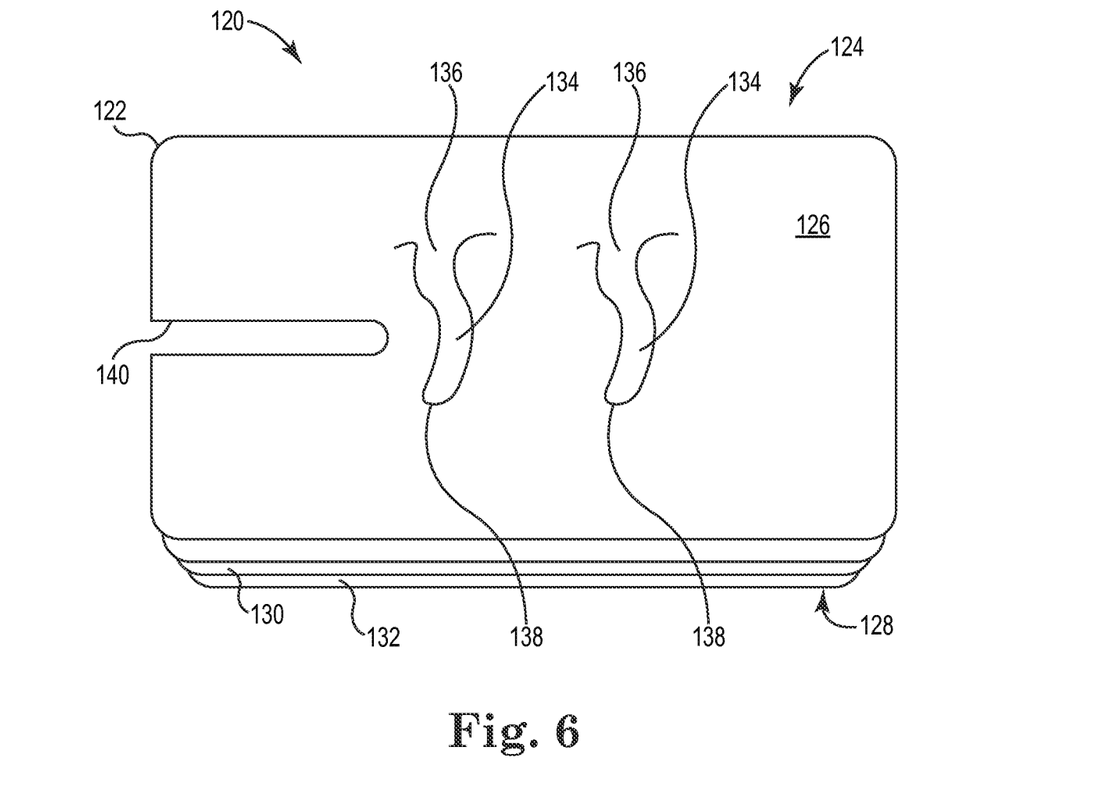
FIG. 6 is a perspective view of a fixation device in accordance with embodiments of the present invention.

FIG. 6 is a perspective view of a fixation device 120 that includes a polymeric device body 122. While the polymeric device body 122 is illustrated as having a rectangular profile, it will be appreciated that in some embodiments the polymeric device body 122 may have a square profile, a round profile or another, irregular, shape. The polymeric device body 122 includes a base 124 having an upper surface 126 and a lower surface 128. In some embodiments, the lower surface 128 includes an adhesive coating or layer 130 that can be used to secure the polymeric device body 130 onto the patient P proximate the entry point. Any suitable dermatologically safe adhesive can be used. In some embodiments, a peel-away layer 132 may be disposed over the adhesive layer 130 to protect the adhesive layer 130 until the fixation device 120 is about to be used. In some embodiments, the base 124 may be configured to accommodate sutures to provide additional securement.

In some embodiments, as illustrated, the fixation device 120 includes a pair of resilient fingers 134. The resilient fingers 134 can be integrally molded as a unitary portion of the polymeric device body 122, and accordingly may be part of the upper surface 126. Each resilient finger 134 can have an attachment portion 136 and a remote end 138. It will be appreciated that while a pair of resilient fingers 134 are illustrated, in some embodiments the fixation device 120 may include only a single resilient finger 134, or may include three or more resilient fingers 134.

The resilient fingers 134 are biased into a position in which the remote ends 138 of each resilient finger 134 are in contact with the upper surface 126. In order to fixate the lead 14, each of the remote ends 138 of the resilient fingers 134 can be lifted or otherwise moved away from the upper surface 126, the lead 14 can be disposed under the resilient finger 134, and then each resilient finger 134 can be permitted to return to its biased position against the upper surface 126, thereby holding the lead 14 in place. In some embodiments, the fixation device 120 includes a slot 140 (or a hole) to facilitate placement of the fixation device 120 relative to the lead 14. In some embodiments, the upper surface 126 may include additional structure (not illustrated) such as tabs to engage the remote ends 138 of the resilient fingers 134.

Figure 7:
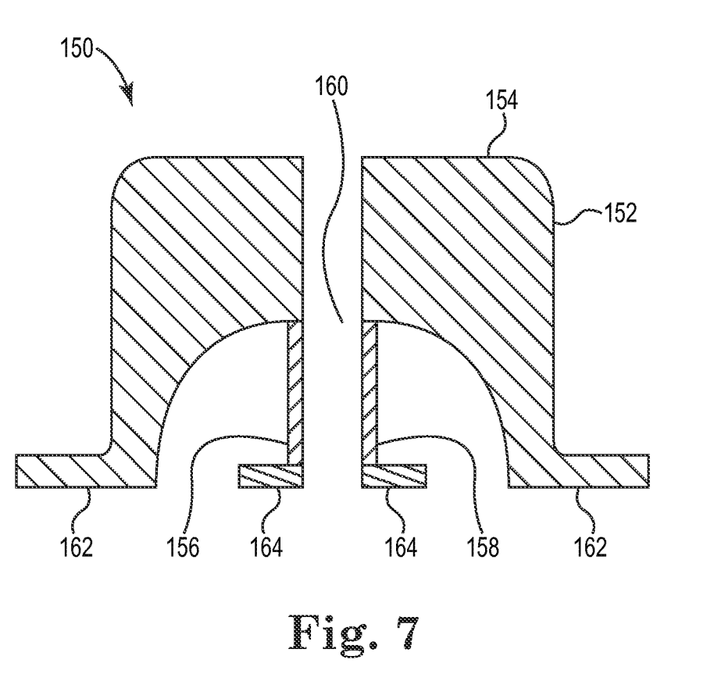
FIG. 7 is a schematic cross-sectional view of a fixation device in accordance with embodiments of the present invention.

FIG. 7 is a schematic cross-sectional view of a fixation device 150 that includes a polymeric device body 152. The polymeric device body 152 includes an upper portion 154, a lower portion 156 and polymeric bands 158 that extend between the upper portion 154 and the lower portion 156. In some embodiments, the upper portion 154, the lower portion 156 and the polymeric bands 158 may be molded of the same material. In some embodiments, the upper portion 154, the lower portion 156 and the polymeric bands 158 may be molded of different materials. A lumen 160 that is sized to accommodate the lead 14 extends between the polymeric bands 158.

In some embodiments, the upper portion 154 may be rotatable relative to the lower portion 156. By placing the lead 14 through the lumen 160, and then rotating the upper portion 154 relative to the lower portion 156, the polymeric bands 158 will tighten around the lead 14, thereby securing the lead 14 in position as well as sealing around the lead 14 to reduce the possible risk of infection. In some embodiments, each of the upper portion 154 and the lower portion 156 include an attachment portion 162, 164, respectively, that can include an adhesive layer for securing each of the upper portion 154 and the lower portion 156 to the patient P once the polymeric bands 158 have been tightened against the lead 14.

Figure 8:
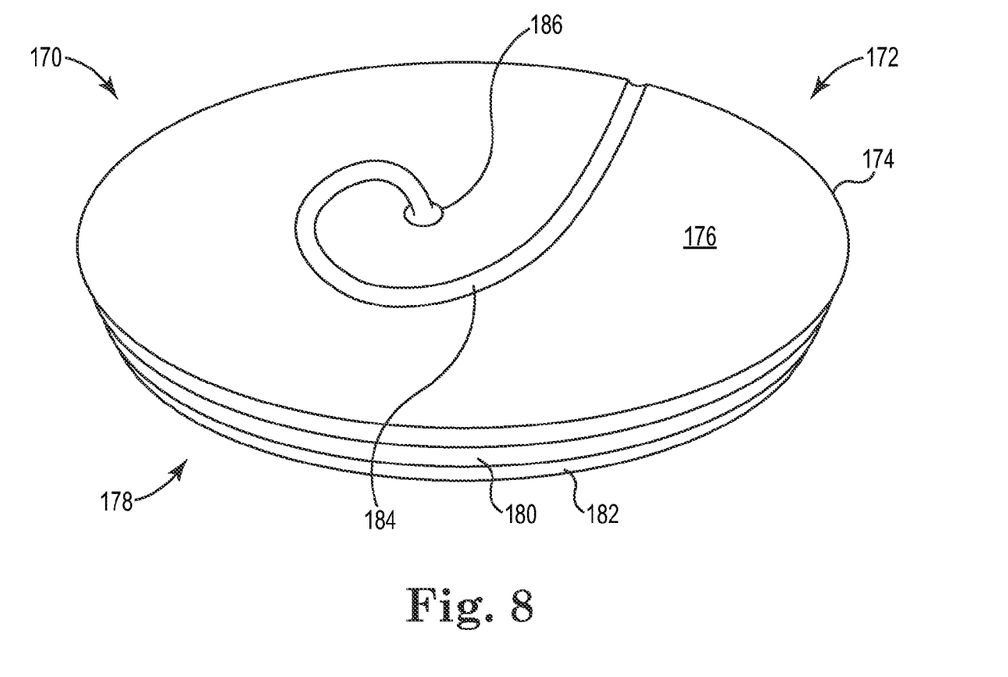
FIG. 8 is a schematic view of a fixation device in accordance with embodiments of the present invention.

FIG. 8 is a perspective view of a fixation device 170 that includes a polymeric device body 172. While the polymeric device body 172 is illustrated as having an ovoid profile, it will be appreciated that in some embodiments the polymeric device body 172 may have a square profile, a round profile or another, irregular, shape. The polymeric device body 172 includes a base 174 having an upper surface 176 and a lower surface 178. In some embodiments, the lower surface 178 includes an adhesive coating or layer 180 that can be used to secure the polymeric device body 172 onto the patient P proximate the entry point. Any suitable dermatologically safe adhesive can be used. In some embodiments, a peel-away layer 182 may be disposed over the adhesive layer 180 to protect the adhesive layer 180 until the fixation device 170 is about to be used. In some embodiments, the fixation device 170 may include a slot to facilitate advancement of the lead 14.

In some embodiments, as illustrated, the upper surface 176 includes a channel 184 that is molded or otherwise formed into the upper surface 176. The channel 184 is configured to frictionally engage the lead 14. The channel 184 leads to an aperture 186 that is configured to permit the lead 14 to extend through the aperture 186 and into the patient P. In some embodiments, an additional cover may fit onto the polymeric device body 172.

Figure 9:
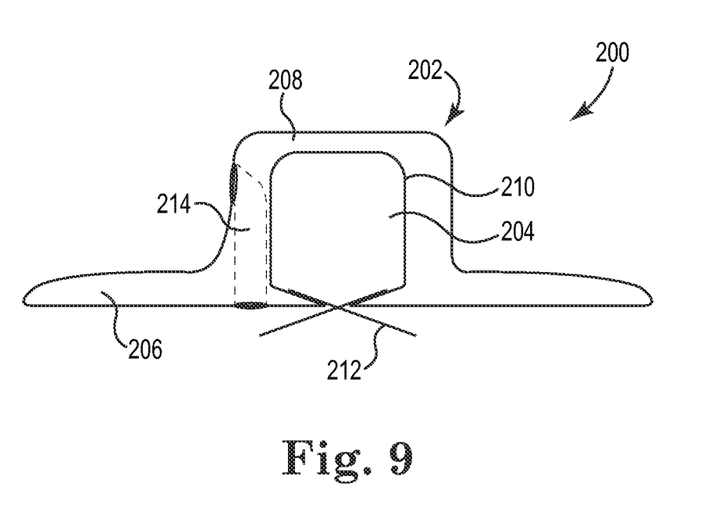
FIG. 9 is a schematic view of a fixation device in accordance with embodiments of the present invention.

FIG. 9 is a schematic view of a fixation device 200 that includes a polymeric device body 202 and a fixation member 204 that is disposed within the polymeric device body 202. The polymeric device body 202 includes a base portion 206 and a raised portion 208. The base portion 206 may, in some embodiments, include an adhesive layer for fixation to the patient. The raised portion 208 includes a lumen 214 extending through the raised portion 208 to accommodate the lead 14. The raised portion 208 also includes part of the fixation member 204. The fixation member 204 includes an activation portion 210 that can be squeezed or otherwise manipulated to move an under skin fixation feature 212 into a position in which the under skin fixation feature 212 can be inserted into the patient P. Once inserted, the activation portion 210 may be released, allowing the under skin fixation feature 212 to revert to a biased position securing the fixation device 200 to the patient P.

In some embodiments, as illustrated, the fixation member 204 (and the activation portion 210) may be at least substantially perpendicular to the patient's skin. In some embodiments, the fixation member 204 may be positioned parallel, or substantially parallel, to the patient's skin in order to provide a lower profile. While not illustrated, in some embodiments the fixation member 204 may be configured to secure the lead 14 to the fixation device 200 via a frictional fit when the activation portion 210 is squeezed and released.

Figure 10:
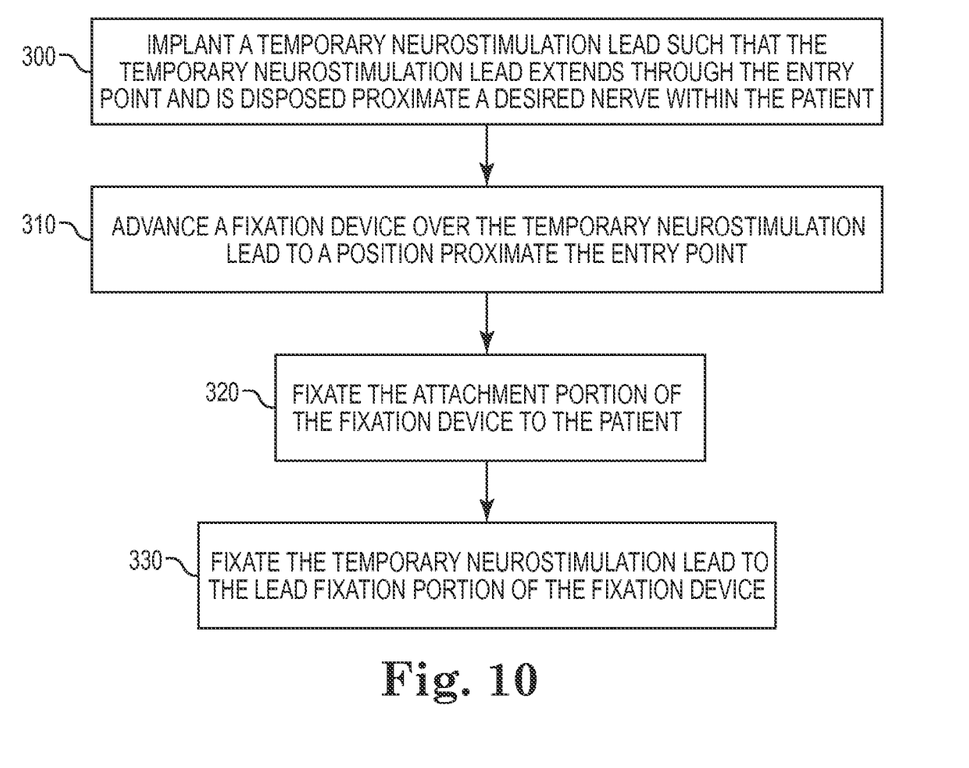
FIG. 10 is a flow diagram illustrating a method in accordance with embodiments of the present invention.

FIG. 10 is a flow diagram providing an illustrative but non-limiting example of a method in accordance with embodiments of the present invention. A temporary neurostimulation lead may be implanted within the patient such that the temporary neurostimulation lead extends through the entry point and is disposed proximate a desired nerve within the patient as generally indicated at block 300. As generally shown at block 310, a fixation device may be advanced over the implanted lead to a position that is near the entry point. An attachment portion of the fixation device may be adhesively fixated to the patient as shown at block 320.

The temporary neurostimulation lead may be fixated to a lead fixation portion of the fixation device, as generally indicated at block 330. In some embodiments, fixating the lead includes fitting the lead into a curved channel formed in the fixation device. In some embodiments, fixating the lead includes placing the lead under one or more resilient fingers that are formed as part of the fixation device. In some embodiments, fixating the lead includes using an external clamp on the fixation device. In some embodiments, fixating the lead includes rotating an upper portion of the fixation device relative to a lower portion of the fixation device.

Figure 11:
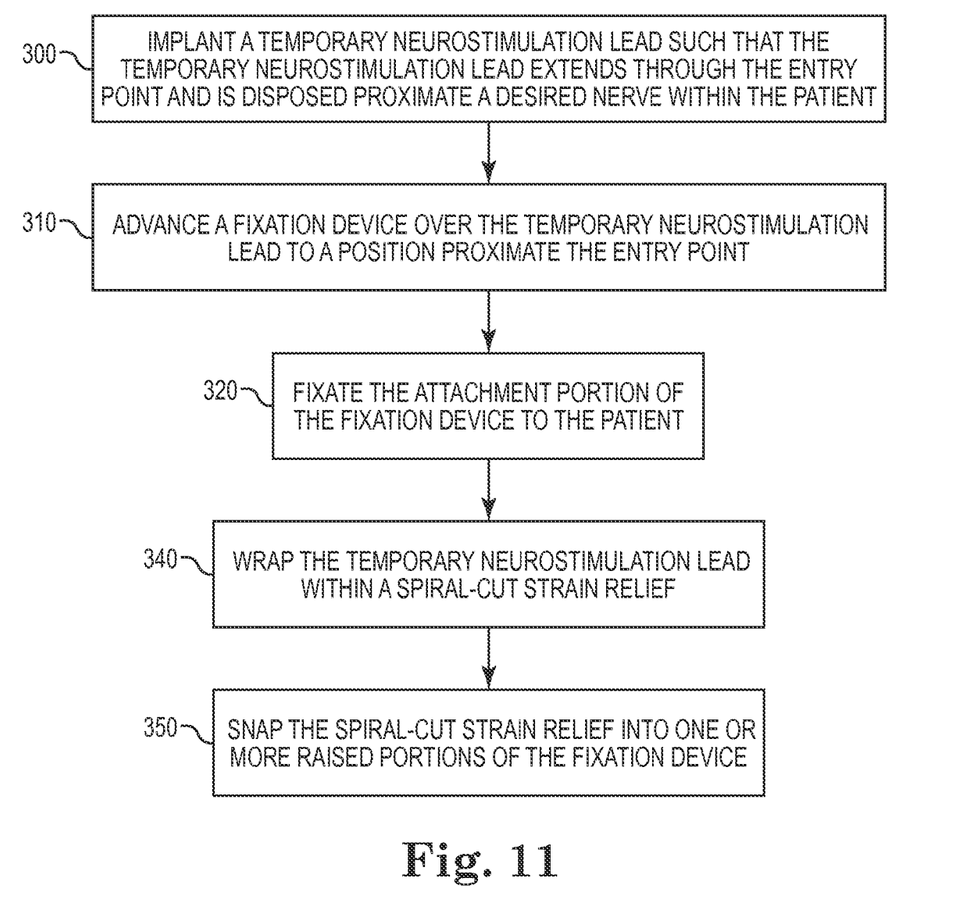
FIG. 11 is a flow diagram illustrating a method in accordance with embodiments of the present invention.

FIG. 11 is a flow diagram providing an illustrative but non-limiting example of a method in accordance with embodiments of the present invention. A temporary neurostimulation lead may be implanted within the patient such that the temporary neurostimulation lead extends through the entry point and is disposed proximate a desired nerve within the patient as generally indicated at block 300. As generally shown at block 310, a fixation device may be advanced over the implanted lead to a position that is near the entry point. An attachment portion of the fixation device may be adhesively fixated to the patient as shown at block 320.

The temporary neurostimulation lead may be wrapped around or within a spiral-cut strain relief member as generally indicated at block 340. As shown at block 350, the spiral-cut strain relief member may be snapped or otherwise fitted into one or more raised portions of the fixation device in order to secure the lead relative to the patient P as well as to provide a strain relief function.

The fixation devices described herein, including the fixation device 30, the fixation device 40, the fixation device 80, the fixation device 120, the fixation device 150, the fixation device 170 and the fixation device 200 may be formed of a variety of different materials. In some embodiments, at least some of these fixation devices 30, 40, 80, 120, 150, 170 and 200 may be formed of waterproof materials. In some embodiments, at least some of these fixation devices 30, 40, 80, 120, 150, 170 and 200 may be formed of breathable materials. In some instances, antibacterial agents may be applied to or incorporated into at least some of the fixation devices 30, 40, 80, 120, 150, 170 and 200.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. A method of securing a temporary neurostimulation lead relative to an entry point on a patient, the method comprising:
    implanting the temporary neurostimulation lead within the patient such that the temporary neurostimulation lead extends through the entry point and is disposed proximate a desired nerve within the patient;
    advancing a fixation device over the temporary neurostimulation lead to a position proximate the entry point, the fixation device including an attachment portion configured to be releasably fixated to the patient and a lead fixation portion configured to secure the temporary neurostimulation lead, the lead fixation portion comprising one or more raised portions that are configured to frictionally engage a spiral-cut strain relief element having a groove around a circumference and continuous along a length of the strain-relief element;
    adhesively fixating the attachment portion of the fixation device to the patient; and
    fixating the temporary neurostimulation lead to the lead fixation portion of the fixation device by wrapping the temporary neurostimulation lead within the groove of the spiral-cut strain relief snapping the spiral-cut strain relief into the one or more raised portions.

2. The method of claim 1, wherein the lead fixation portion comprises a curved channel formed in an upper surface of the lead fixation portion, and fixating the temporary neurostimulation lead to the lead fixation portion of the fixation device comprises fitting the temporary neurostimulation lead into the curved channel.

3. The method of claim 1, wherein the lead fixation portion comprises an upper surface and one or more resilient fingers extending from the upper surface and biased into contact with the upper surface, and fixating the temporary neurostimulation lead to the lead fixation portion of the fixation device comprises:
    lifting each of the one or more resilient fingers;
    placing the temporary neurostimulation lead under each of the one or more resilient fingers; and
    allowing each of the one or more resilient fingers to return to their biased position in contact with the upper surface.

4. The method of claim 1, wherein the lead fixation portion comprises a resilient polymeric body including a lumen therethrough to accommodate the temporary neurostimulation lead, and advancing the fixation device over the temporary neurostimulation lead to a position proximate the entry point comprises advancing the fixation device over the temporary neurostimulation lead with the temporary neurostimulation lead extending through the lumen.

5. The method of claim 4, wherein fixating the temporary neurostimulation lead to the lead fixation portion of the fixation device comprises disposing an external clamp over the resilient polymeric body to compress the resilient polymeric body into frictional contact with the temporary neurostimulation lead.

6. The method of claim 4, wherein the resilient fixation portion comprises an upper portion that is rotatable relative to a lower portion, and the lumen is defined at least in part by polymeric bands extending between the upper portion and the lower portion, and fixating the temporary neurostimulation lead to the lead fixation portion of the fixation device comprises:
   rotating the upper portion relative to the lower portion in order to tighten the polymeric bands around the temporary neurostimulation lead; and
   securing the upper portion relative to the lower portion to maintain the polymeric bands in their tightened configuration.

7. The method of claim 4, wherein the lead fixation portion comprises an under skin fixation feature and an activation portion that is operably connected to the under skin fixation feature, and adhesively fixating the attachment portion of the fixation device to the patient further comprises:
   squeezing the activation portion to move the under skin fixation feature into a configuration that permits the under skin fixation feature to be inserted under the skin;
   inserting the under skin fixation feature under the skin; and
   releasing the activation portion to permit the under skin fixation feature to return to a biased position that anchors the under skin fixation feature under the skin.

8. A fixation device configured to releasably secure a temporary neurostimulation lead relative to an entry point on a patient, the device comprising:
   a polymeric device body having a lower surface and a upper surface;
   a dermatologically safe adhesive disposed on the lower surface for releasably securing the fixation device to the patient proximate the entry point;
   a strain relief member arranged on the upper surface of the polymeric device body and having a groove configured to engage the temporary neurostimulation lead within the groove, the groove being spirally arranged around a circumference and continuous along a length of the strain relief member; and
   a lead fixation structure formed on the upper surface having a curved channel configured to frictionally engage with the strain relief member to releasably secure the temporary neurostimulation lead.

9. The fixation device of claim 8, wherein the groove has a width approximately equal to a diameter of the temporary neurostimulation thereby allowing the temporary neurostimulation to wind into the groove and provide at least some resistance to removal of the temporary neurostimulation.

10. The fixation device of claim 8, wherein the lead fixation structure comprises one or more raised portions that are configured to frictionally engage the temporary neurostimulation lead.

11. The fixation device of claim 10, wherein the groove has a depth from approximately 10 percent to approximately 40 percent of a diameter of the strain relief member.

12. The fixation device of claim 8, wherein the lead fixation structure comprises one or more resilient fingers that extend from the upper surface and are biased into contact with the upper surface.

13. The fixation device of claim 8, further comprising an external clamp that is configured to clamp onto the lead fixation structure to releasably secure the temporary neurostimulation lead.

14. The device of claim 8, wherein the polymeric device body comprises an upper portion that is rotatable relative to a lower portion, with polymeric bands extending between the upper portion and the lower portion, and wherein rotating the upper portion relative to the lower portion enables the polymeric bands to tighten around the temporary neurostimulation lead.

15. The device of claim 8, further comprising an under skin fixation element and an activation portion that is operably connected to the under skin fixation element, and wherein squeezing the activation portion moves the under skin fixation element into a configuration that permits the under skin fixation element to be inserted under the skin and releasing the activation portion permits the under skin fixation element to return to a biased position that anchors the under skin fixation element under the skin.

16. A fixation device configured to releasably secure a temporary neurostimulation lead relative to an entry point on a patient, the device comprising:
   a polymeric device body having a lower surface and an upper surface;
   a dermatologically safe adhesive disposed on the lower surface for releasably securing the fixation device to the patient proximate the entry point;
   a spiral-cut strain relief element including an elongate body and a spiral groove formed within the elongate body, the spiral groove arranged around a circumference and continuous along a length of the strain-relief element and configured to accommodate the temporary neurostimulation lead therein; and
   a pair of raised portions molded into the upper surface, the pair of raised portions being configured to frictionally engage the spiral-cut strain relief element.

17. The fixation device of claim 16, further comprising a peel away layer disposed on the dermatologically safe adhesive in order to protect the adhesive.

18. The fixation device of claim 16, wherein the pair of raised portions are integrally molded as part of the polymeric device body.

19. The fixation device of claim 16, wherein the polymeric device body includes an elongate slot formed within the polymeric device body such that the elongate slot permits the fixation device to be slid laterally onto the temporary neurostimulation lead.

* * * * *